(12) United States Patent
Lüning et al.

(10) Patent No.: US 11,103,675 B2
(45) Date of Patent: Aug. 31, 2021

(54) URINARY CATHETER

(71) Applicant: Saxonia R + D GmbH & Co. KG, Radeberg (DE)

(72) Inventors: Rudolph Lüning, Dresden (DE); Larry Purcell, Radeberg (DE); Manfred Wirth, Dresden (DE)

(73) Assignee: Saxonia R + D GmbH & Co. KG, Radeberg (DE)

( * ) Notice: Subject to any disclaimer, the term of this patent is extended or adjusted under 35 U.S.C. 154(b) by 296 days.

(21) Appl. No.: 16/091,999

(22) PCT Filed: Apr. 6, 2017

(86) PCT No.: PCT/EP2017/058240
§ 371 (c)(1),
(2) Date: Oct. 8, 2018

(87) PCT Pub. No.: WO2017/174715
PCT Pub. Date: Oct. 12, 2017

(65) Prior Publication Data
US 2019/0091440 A1 Mar. 28, 2019

(30) Foreign Application Priority Data

Apr. 7, 2016 (DE) .......................... 102016205834.7
Feb. 28, 2017 (DE) .......................... 202017101126.7

(51) Int. Cl.
*A61M 25/00* (2006.01)
*A61M 25/10* (2013.01)

(52) U.S. Cl.
CPC .... *A61M 25/0017* (2013.01); *A61M 25/0068* (2013.01); *A61M 25/10* (2013.01);
(Continued)

(58) Field of Classification Search
CPC .............. A61M 25/00; A61M 2205/00; A61M 2025/0057; A61M 2025/105;
(Continued)

(56) References Cited

U.S. PATENT DOCUMENTS 3,394,705 A * 7/1968 Abramson ........ A61M 25/0017
604/43
3,593,713 A * 7/1971 Bogoff .............. A61M 25/0017
604/102.02
(Continued)

FOREIGN PATENT DOCUMENTS

DE     102005013130 A1    9/2006
DE     202007007713 U1    9/2008
(Continued)

*Primary Examiner* — Adam Marcetich
(74) *Attorney, Agent, or Firm* — Michael Soderman (57) ABSTRACT

The invention relates to urinary catheters having a catheter tube with a first connection on the distal end and at least one catheter eye to be positioned in the urinary bladder. The urinary catheters are distinguished in particular in that they may be used problem-free as indwelling catheters.
To this end, disposed in the urinary bladder is a reservoir container that is connected via a channel running parallel to the catheter tube to a second connection as distal end of the channel. In addition, the channel is connected to the urethra via at least one opening of the channel wall.

12 Claims, 3 Drawing Sheets

(52) U.S. Cl.
CPC ............... *A61M 2205/0205* (2013.01); *A61M 2205/3327* (2013.01); *A61M 2205/3344* (2013.01); *A61M 2205/3368* (2013.01); *A61M 2205/3379* (2013.01); *A61M 2205/3523* (2013.01); *A61M 2210/1089* (2013.01)

(58) Field of Classification Search
CPC .............. A61M 25/10; A61M 25/0043; A61M 25/0068; A61M 2205/3344; A61M 25/0017; A61M 2210/1089; A61M 2025/1013; A61M 25/1009; A61M 2025/1059; A61M 2025/1061; A61M 2025/1072; A61M 2025/1095; A61M 2025/1097

See application file for complete search history.

(56) References Cited

U.S. PATENT DOCUMENTS

| | | | | |
|---|---|---|---|---|
| 3,807,408 A | * | 4/1974 | Summers | A61M 25/0017 604/104 |
| 3,981,299 A | * | 9/1976 | Murray | A61M 25/0017 604/43 |
| 4,623,329 A | * | 11/1986 | Drobish | A61L 29/16 604/265 |
| 5,007,897 A | * | 4/1991 | Kalb | A61M 25/0043 604/102.02 |
| 5,250,029 A | * | 10/1993 | Lin | A61M 25/0017 604/103.11 |
| 5,269,755 A | * | 12/1993 | Bodicky | A61M 25/0017 604/103.01 |
| 5,417,657 A | | 5/1995 | Hauer | |
| 5,419,763 A | * | 5/1995 | Hildebrand | A61M 25/1011 604/101.03 |
| 5,562,652 A | * | 10/1996 | Davis | A61L 29/16 604/103.03 |
| 6,955,661 B1 | * | 10/2005 | Herweck | A61L 29/041 604/264 |
| 2002/0077594 A1 | * | 6/2002 | Chien | A61M 25/10 604/103.02 |
| 2002/0133140 A1 | * | 9/2002 | Moulis | A61M 25/10 604/508 |
| 2004/0186538 A1 | * | 9/2004 | Eshel | A61B 18/04 607/105 |
| 2005/0085777 A1 | * | 4/2005 | Tan | A61L 29/16 604/265 |
| 2006/0079727 A1 | * | 4/2006 | Chernomorsky | A61M 25/1002 600/3 |
| 2008/0015540 A1 | * | 1/2008 | Muni | A61B 17/3421 604/500 |
| 2008/0114286 A1 | * | 5/2008 | Hamel | A61N 1/327 604/21 |
| 2008/0300571 A1 | * | 12/2008 | LePivert | A61B 18/1492 604/503 |
| 2010/0298757 A1 | * | 11/2010 | Frigstad | A61M 25/10 604/20 |
| 2013/0331818 A1 | * | 12/2013 | Buysman | A61M 31/00 604/506 |
| 2014/0007956 A1 | * | 1/2014 | Rutty | A61B 5/064 137/551 |
| 2015/0359996 A1 | * | 12/2015 | Arora | A61B 5/14507 600/301 |

FOREIGN PATENT DOCUMENTS

| | | | | |
|---|---|---|---|---|
| DE | 202011104675 U1 | 9/2012 | | |
| DE | 202012006814 U1 | 9/2012 | | |
| WO | 8903232 A1 | 4/1989 | | |
| WO | WO-8903232 A1 | * 4/1989 | ............ | A61K 9/0024 |
| WO | 03033045 A2 | 4/2003 | | |
| WO | 2015191125 A1 | 12/2015 | | |

* cited by examiner

URINARY CATHETER

CROSS REFERENCE TO RELATED APPLICATIONS

This application is the U.S. national stage of International Application No. PCT/EP2017/058240, filed on Apr. 6, 2017. The international application claims the priority of DE 102016205834.7 filed on Apr. 7, 2016 and the priority of DE 202017101126.7 filed on Feb. 28, 2017; all applications are incorporated by reference herein in their entirety.

BACKGROUND

The invention relates to a urinary catheter having a catheter tube with a first connection at the distal end and at least one catheter eye to be positioned in the bladder.

Urinary catheters are instruments commonly used in medicine for draining the bladder (of urine) via the urethra (transurethral) or the abdominal wall. A distinction is made between straight catheters and indwelling catheters. The latter are designed to remain in the urethra and/or bladder for an extended period and drain urine from the bladder continuously or temporarily. Catheters are used not only for interventions that relate to the urinary passages and/or the bladder or the prostate, but are also very often used post-surgically when it may be anticipated that the patient will not be able to stand up for a period of time or when a precise accounting of fluids is required.

As a rule, indwelling catheters are embodied as two-way catheters, which means that, in addition to having a channel for draining urine, the catheter tube has a second channel via which a balloon in the bladder at the end of the catheter may be filled with fluid. The filled balloon holds the catheter in place in the bladder.

Primarily saline solution or glycerine or glycerine solution is used as the fluid for filling the balloon. Three-way catheters are also used; in these, the catheter tube has a third channel with an outlet opening at the end of the catheter and through which an irrigation solution, for example, or a medication may be added to the bladder. Like the urine, the irrigation solution leaves the bladder through the primary channel through an opening at the end of the catheter, also called the catheter eye.

DE 20 2012 006 814 U1 relates to a urinary catheter having a tube, wherein the tube has an insertion section for inserting into a urinary bladder through a urethra and wherein the tube has a connection section for connecting connection elements and wherein fluid may be drained from the urethra at the connection section via the insertion section. A closable valve is arranged the connection section in such a way that the fluid may be prevented from escaping from the connection section when the valve is closed. Thus, when the valve is closed, a full urine bag may be changed without urine being able to escape from the connection section of the urinary catheter.

Known from DE 20 2007 007 713 U1 is a multichannel catheter that is distinguished from the known catheters in that the catheter body has at least a third channel, for applying at least one medication, parallel to the catheter body with at least one outlet opening. After the catheter has been inserted into the urinary bladder, medications may be specifically applied in the region of the urethra via the third channel of the catheter using this outlet opening.

DE 10 2005 013130 A1 discloses a catheter, the tube of which has a surface that, at least in regions, has a structure or contour suitable for receiving a lubricant so that the structure acts as a depot for a lubricant. This is intended to keeping injury to the mucosa to a minimum when the catheter is inserted.

Known from DE 20 2011 104 675 U1 is a transurethral indwelling catheter for treating dysfunctions of the bladder and/or prostate. The indwelling catheter comprises a catheter tube, a bladder balloon and a prostate balloon having corresponding supply and drainage lines. The urine drainage opening is arranged above, and necessitated by anatomy, the prostate balloon is arranged below the bladder balloon. The walls of the bladder and prostate balloon are embodied such that fluids containing medications and stored in the balloons may diffuse into the bladder or prostate in a targeted manner. When filled, the prostate balloon has a maximum outer diameter between 20 and 30 Charr. The indwelling catheter should have a 48-hour maximum dwell time in the bladder. It is a drawback that these catheters may be used only in males. In addition, it must be assumed that the disclosed balloon strength is selected essentially too low to hold the catheter in the bladder.

Use of catheters may lead to complications. One known problem is the occurrence of bacterial infections, which occur primarily in patients who have to use an indwelling catheter. The risk of bacteriuria increases if the catheter remains in the body for longer than 7 days. The bacteria travel through the urethra into the bladder. This condition may be detected when bacteria are found in the urine. Healthy urine is sterile.

This is promoted by the type and/or shape of the catheter. The bladder is never completely emptied because of the arrangement of the catheter eyes at the end of the catheter over the balloon, which ensures the catheter is seated securely in the bladder. Residual urine, in which salts, such as for example calcium salts, and urine concentrate always remains in the bladder. After a few days various compounds crystallize. These crystals cause pain due to the mechanical friction on the inner wall of the urethra and bladder; in addition, the crystals may leave the bladder along the catheter and migrate into the urethra.

The normally moist urethral wall may dry off or dry out due to the catheter. A urethra that is not optimally moistened may lead to painful irritations due to the mechanical friction between catheter wall and urethral wall. Moreover, a nutrient medium for microbes and bacteria may form, so that inflammation may occur between the catheter wall and the wall of the urethra. Such infections may create scar tissue in the urethra and urethral strictures and may be extremely difficult to cure over time.

SUMMARY

The invention relates to urinary catheters having a catheter tube with a first connection on the distal end and at least one catheter eye to be positioned in the urinary bladder.

The urinary catheters are distinguished in particular in that they may be used problem-free as indwelling catheters.

To this end, disposed in the urinary bladder is a reservoir container that is connected via a channel running parallel to the catheter tube to a second connection as distal end of the channel. In addition, the channel is connected to the urethra via at least one opening of the channel wall.

DETAILED DESCRIPTION

The underlying object of the invention specified in claim 1 is to provide in particular a urinary catheter as an indwelling catheter that is low-irritating and relatively painless.

This object is attained with the features listed in claim 1.

The urinary catheters having a catheter tube with a first connection at the distal end and at least one proximal catheter eye are distinguished in particular in that they may be used problem-free as indwelling catheters.

To this end, disposed in the bladder is a reservoir container that is connected via a channel to a second connection as the distal end of the channel. Moreover, the channel is connected to the urethra via at least one opening in the channel wall.

The inventive urinary catheter may be inserted via the urethra into the bladder (transurethral) or may be inserted into the bladder via the abdomen as a suprapubic urinary catheter.

The catheter tube is a hollow and flexible line through which a fluid, for example, may be transported. This hollow line is also called the lumen. The catheter tube is delimited by an outer wall that may be designed with different thicknesses. The catheter tube may advantageously comprise a metal or a polymer. These may be stainless steel, silicone, latex, polyvinyl chloride, polyethylene, and/or polyurethane. Advantageously, any common, biocompatible material may be used so that there are no undesired reactions when using the catheter in the body. In addition, the catheter tube may contain other materials or be coated with other materials in order to impart, for example, hydrophilic properties for better sliding and/or for better contrasting properties during X-ray imaging.

The first connection at the distal end is a connection that is disposed on the end of the catheter away from the body, that is, at the end that is not disposed in the body after the catheter has been inserted. The connection may be any known connection. For example, a connection may be used to connect different bags for collecting urine.

Another flexible and hollow line through which a fluid may be transported is also called a channel. The channel, also called a lumen, preferably runs parallel on or in the catheter tube.

The channel has at least one opening that connects the interiors of the channel and the urethra. After the catheter has been inserted into the bladder, this opening is preferably an outlet opening below the sphincter muscle of the bladder in the region of the urethra.

The channel may be arranged on or in the catheter tube. If the channel is disposed in the catheter tube, the opening is an opening that transects the channel wall and the catheter tube wall. At least the regions of the walls around the opening are connected to one another so that fluid from the reservoir container can travel only into the urethra and not into the catheter tube.

Once the reservoir container has been filled with fluid, the second connection is closed so that the fluid remains in the reservoir container. Through the opening disposed on the channel, fluid may travel out of the reservoir container via the channel to the opening. From the latter it flows into the interior space between urethra and either catheter tube or catheter tube with channel. Thus fluid advantageously travels continuously out of the opening, so that the region between the catheter and urethra is kept moist continuously. Crystals that may form due to concentrated or concentrating urine, and/or bacteria that may form colonies on these nutrient media between catheter and urethral wall, may thus be prevented from growing, and may be moistened continuously and/or flushed away and carried out of the body. In addition, infections may be reduced or avoided.

Advantageously, inventive catheters for transurethral use that are intended for use in men have the outlet opening. Continuous moistening and/or flushing is particularly important because the urethra in a man is significantly longer than in a woman.

The length of the catheter tube of the urinary catheter may be selected individually. If the catheter is intended for use in a man, the catheter tube is embodied longer than in an catheter according to the invention for a woman.

The fluid for the reservoir container may be at least one solution containing medication and/or a substance affecting cell nutrition. This is preferably a substance selected from water, glycerine, and a bacteriostatic and/or bactericidal substance. In one special embodiment, the fluid contains at least one substance that counteracts formation of crystals, for example urinary crystals. Moreover, it may advantageously be an anti-inflammatory agent.

The opening may be a perforation that goes through the material of the channel. The perforation preferably has a diameter of 0.1 mm to 5 mm, especially 0.5 mm to 1 mm. In one embodiment, the material of the channel may have a plurality of perforations, wherein a plurality of perforations are disposed adjacent to or among one another.

In another embodiment, the at least one perforation may be coated with a nano mesh. A nano mesh here is an inorganic, two-dimensional nano-structured material.

An opening in the wall of the catheter tube, through which opening, after the catheter has been inserted into the bladder, urine is transported out of the bladder via the lumen of the catheter tube using the first distal connection, is called the catheter eye. The first distal connection preferably has a bag for collecting the urine. It is advantageously assured that the bladder can be completely emptied by the catheter due to the deep positioning of the catheter eye. No old urine is retained in which salts, such as, for example, calcium salts, or urea may concentrate and crystallize. Thus a situation in which crystals migrate between catheter tube and urethra, and there may cause painful friction and/or a nutrient medium for bacteria, is prevented.

The catheter eye may in principle be embodied in any shape or size. The catheter eye is preferably round to oval and does not have any sharp edges. The oval catheter eye preferably has a maximum diameter, measured across the widest point of the catheter eye, of 1 mm to 10 mm, in particular 1 mm to 5 mm.

Prior to removal from the body, the reservoir should always be emptied, and this is possible at any time using the second connection.

The subordinate claims provide advantageous embodiments of the invention.

According to a refinement of claim 2, the reservoir container may simultaneously be a retention device of the urinary catheter. The filled reservoir container prevents the urinary catheter from slipping out of the body. This is a simple and economically beneficial embodiment of the urinary catheter. In this case, a maximum of two supply lines are to be led through the urethra. Moreover, according to a further embodiment, the proximal reservoir container may be disposed above a proximal retention unit on the catheter tube or surrounds the proximal retention unit, at least in regions. The retention unit may also and in particular be a balloon-type retention unit.

According to the refinement in claim 3, the reservoir container and the retention unit are a balloon-type hollow body that is itself simultaneously a retention unit or that is disposed above the proximal retention unit on the catheter tube.

The reservoir container may advantageously comprise an elastic and flexible material that can contract back to at least approximately its original condition. It is for example latex, silicone, polyurethane, and/or coated materials, such as, for example, silicone-coated latex or polyurethane.

The unfilled reservoir container is advantageously positioned closely against the catheter tube so that it does not interfere or cause pain when the catheter is inserted. The reservoir container is filled via the channel in that fluid may be added, for example, with a syringe via the second connection. After filling, the reservoir container is round to oval. In general, however, the reservoir container may assume any shape. The material of the reservoir container is not permeable.

If the reservoir container is filled, it expands enough that it can accommodate all of the fluid.

The proximal reservoir container may be embodied as a balloon that surrounds the proximal retention device. This construction is advantageously achieved in that the surface area of the balloon disposed in the bladder is reduced. Due to the smaller surface area there is less balloon material surface area available for potential bacterial colonization.

To remove the catheter from the body, each of the balloons must be emptied, which may be done at any time via the appropriate connection.

Moreover, the retention device may also be a different type of retention apparatus for retaining the catheter in the bladder, in which the retention apparatus has at least one notch. At least one catheter eye is advantageously disposed in the notch, so that the bladder may be emptied completely.

According to the refinement in claim 4, disposed between catheter tube with the channel and urethra, at least in regions, is a permeable membrane, a semipermeable membrane, a sponge-like material, a film having perforations, or a combination thereof, wherein fluid travels via the opening as a perforation, when the second connection is closed, out of the reservoir container into the permeable membrane, the semipermeable membrane, the sponge-like material, the film having perforations, or the combination thereof.

The membrane is provided with at least one opening, in particular with a plurality of openings that are arranged statistically distributed across the entire surface area of the membrane. The membrane surrounds the section of the catheter tube that is disposed in the urethra after the catheter has been inserted, and in particular the membrane surrounds the entire length of the section of the catheter tube itself, or of the catheter tube with the channel, disposed in the urethra after the catheter has been inserted.

In conjunction with a catheter tube embodied from a flexible material, the membrane represents a cushion so that pressure necroses and/or injuries to the urethra may be prevented. To this end, the membrane may have air and/or fluid from the reservoir container.

The catheter tube is covered by the membrane or sponge-like material, preferably in the entire region of the urethra, but at least in the region of the bulbar urethra.

Thus fluid advantageously travels via the opening into the membrane or the sponge-like material and further on the urethra. Thus moistening of the urethra and the outside of the catheter tube or the catheter tube with the channel is advantageously provided.

Advantageously, the amount of fluid that travels out of the membrane in a certain period of time may be adjusted using the permeability of the membrane and/or the number of openings.

The membrane may comprise any material that meets the requirements according to the invention. For example, it may comprise latex, silicone, polyurethane, polyisoprene, or coated materials, such as for example silicone-coated latex and/or polyurethane. The membrane advantageously comprises a material that does not contain any components that can be flushed out and is chemically compatible with the fluid and with the urethra.

Advantageously, the material of the membrane is flexible, so that a cushioning effect is also attained. The catheter tube may flexibly adapt in the urethra. Sticking to the urethra, which may be dried out, is avoided.

According to the refinement in claim 5, the channel is a first channel. Moreover, the proximal retention unit is a balloon-type hollow body that is connected via a second channel and that has a third connection as its distal end. The second channel may run parallel to the catheter tube or may be disposed in the catheter tube.

This proximal retention unit comprises a flexible material that is attached to the proximal end of the catheter and may be filled using the second channel via a third connection. During filling, the flexible material expands such that it takes the shape of a balloon. Towards the catheter tube, it may have a notch or cut-out so that in cross-section the balloon has the shape of a circular ring interrupted by the notch or cut-out. The catheter tube may have at least one catheter eye in the notch or cut-out so that the bladder may be completely emptied via the catheter tube.

This retention unit is preferably filled with distilled water and/or glycerine. During transurethral use, the filled retention unit is positioned in bladder trigone above the sphincter muscle of the urethra, which fixes the catheter in the bladder.

Any elastic and flexible material that can contract back to at least approximately its original condition is preferred for the material. For example, it may comprise silicone, latex, polyurethane, silicone-coated latex and/or a polymer.

The first channel may be a component of the catheter tube, the first channel and/or the catheter tube having an opening for connecting the urethra to the reservoir container. Moreover, the second channel may also be a component of the catheter tube, the second channel and/or the catheter tube each having at least one opening for connecting the second channel to the proximal retention unit. The channels may be separate tubes on the inner wall of the catheter tube. In addition, wall regions of the catheter tube may simultaneously be wall regions of the channels.

According to the refinement in claim 6, a permeable membrane, a semi-permeable membrane, a sponge-like material, a film having perforations, or a combination thereof, may be disposed, at least in regions, between catheter tube, with the first channel and the second channel, and urethra, wherein fluid travels out of the reservoir container via the opening as a perforation, with the second connection closed, into the permeable membrane, the semi-permeable membrane, the sponge-like material, the film having perforations, or the combination thereof. The opening furthermore connects the first channel to the reservoir container. When the first channel is arranged in the catheter tube, the opening passes through both the wall of the first channel and the catheter tube wall. The walls of the first channel and of the catheter tube are connected to one another, at least in the region of this opening, so that no fluid can travel out of the reservoir container into the catheter tube.

The sponge-like material of the refinements in claims 5 and 6 preferably surrounds the entire length of the section of the catheter tube disposed in the urethra once the catheter has been inserted, but at least surrounds the region of the bulbar urethra.

The sponge-like material may have a closure to the outside so that no fluid can escape in an uncontrolled manner. This may also be a removable closure, so that a controlled flow is permitted.

The sponge-like material may comprise any material. For instance, it may comprise latex, silicone, polyurethane, polyisoprene, hydrogel, or coated materials, such as, for example, silicone-coated latex and/or polyurethane. The sponge-like material advantageously comprises a material that does not contain any components that can be flushed out and is chemically compatible with the fluid and with the urethra. The sponge-like material is advantageously porous, comprising a suitable material that acts as a sterile limit and is thus impermeable for bacteria and microbes.

The material of the sponge-like material is advantageously flexible, so that a cushioning effect is attained and the sponge-like material acts as a cushion. The catheter tube may flexibly adapt to the wall of the urethra. Sticking to and/or washing out of the urethra, which may be dried out, is avoided.

Thus, fluid may advantageously flow via the perforation into the sponge-like material, which soaks up the fluid and thus can continuously moisten the catheter tube disposed in the urethra across its entire length, from the outside, using the channels. Thus moistening of the outside of the catheter tube with the channels and of the entire urethra is advantageously provided.

In one preferred embodiment, the opening, particularly preferably the membrane and/or the sponge-like material, may be equipped with a bactericidal connection, especially a connection containing a noble metal, for example silver.

The opening, preferably the membrane and/or the sponge-like material, may be positioned radially, in a spiral, or flat over the catheter tube. The membrane and/or the sponge-like material is preferably embodied thin enough that it does not cause any pain for the patient when it is inserted and while the catheter remains in the body.

According to the refinement in claim 7, disposed between the openings as first openings is a supply container that surrounds the catheter tube, at least in regions, that is connected to the first channel by two openings, and that has a flexible wall.

According to the refinement in claim 8, the flexible wall of the supply container has, at least in regions, a selectively permeable membrane or a semi-permeable membrane or has perforations. The membrane may comprise, for example, silicone, latex, polyurethane, polyamide, an elastomer, a polyamide, polyvinyl chloride, or a thermoplastic. Moreover, an open-pore flexible body may be disposed in the supply container. It may be a sponge-like material, for instance, as a storage medium.

According to the refinement in claim 9, the catheter eye is disposed at the level of the retention unit. The lower edge of the catheter eye preferably closes with the lower edge of the retention unit, so that, after the catheter has been inserted into the bladder, the catheter eye is positioned directly above the sphincter muscle of the urethra at the floor of the urethra, that is, as deep as possible in the bladder trigone.

In another embodiment, the urinary catheter has a plurality of catheter eyes. These may assume any possible position relative to one another and/or have the same or different shapes and/or sizes. The two catheter eyes are preferably positioned on the same side of the catheter tube above one another or at the same level of the catheter tube on opposing tubes.

In another embodiment, the urinary catheter has at least one proximal catheter eye at the level of the proximal retention unit and at least one catheter eye at the tip of the catheter tube. In this case, the tip of the catheter tube represents the proximal end of the catheter or catheter tube that represents the uppermost point of the catheter after it has been inserted into the bladder. Depending on the individual body structure of the person, this uppermost point is positioned 2 cm to 10 cm above the floor of the bladder. The tip of the catheter may have any shape.

In another embodiment, the catheter tube may have at least one catheter eye that is disposed at the tip of the catheter. A catheter embodied in this manner is advantageously a suprapubic abdominal catheter.

According to the refinement in claim 10, at least one region of the wall of the reservoir container is a selectively permeable membrane or a semi-permeable membrane or the reservoir container or containers has or have at least one outlet, embodied as a perforation, to the bladder and/or catheter tube, wherein the catheter tube also has a through-hole at this location. The interior of the reservoir container is thus connected to the interior of the bladder via the region of the wall of the reservoir container or via the outlet embodied as a perforation.

The fluid may advantageously exit from the reservoir container through the outlet, so that the fluid travels into the bladder. Depending on the composition of the fluid, this makes it possible, for instance, for bacterial substances to be intentionally conducted into the bladder. All of the fluid may advantageously continuously exit from the reservoir container through the outlet.

At least one outlet is preferably embodied as a perforation that is preferably disposed in the upper region of the reservoir container facing the catheter tip. In general, the perforation may be disposed at any desired location in the reservoir container.

In a further embodiment, the reservoir container may have a plurality of perforations that are distributed statistically across the surface of the reservoir container.

Advantageously, it is possible to influence how much fluid leaves the reservoir container in which period of time using the size and/or number of the perforations or the embodiment of the membrane.

According to the refinement in claim 11, the channel terminates in the interior of the bladder, the end being open or having a membrane and/or a non-return device. Thus fluid may also travel out of the reservoir container into the bladder. This may also occur when filling or after filling the reservoir container, of course. The fluid may also contain medications or active substances that may thus travel, with the fluid, into the bladder and into the space between urethra and catheter tube with at least the first channel. The non-return device prevents urine from entering the first channel. It may be a flexible lip, for example, that is automatically pressed by urine in the bladder against the end of the first channel, closing the latter.

According to the refinement in claim 12, the proximal retention unit is embodied in a balloon-type manner, the balloon having a cutout up to the catheter tube so that the cross-section of the balloon is an interrupted ring. The catheter tube furthermore has the catheter eye in the cutout. Thus the bladder may be emptied completely.

According to a further refinement, at least one pressure sensor and/or one temperature sensor and/or one fluid level sensor is disposed in the reservoir container and/or in the catheter tube. This or these is or are connected to a microcontroller of a transponder having a transmitter/receiver and an antenna for electromagnetic waves.

According to a further refinement, at least one moisture sensor that is connected to a microcontroller of a transponder having a transmitter/receiver and an antenna for electromagnetic waves is disposed in the first channel.

According to a further refinement, at least one flow meter sensor that is or are connected to a microcontroller of a transponder having a transmitter/receiver and an antenna for electromagnetic waves is or are disposed in the catheter tube and/or in the first channel.

The measured values of the specific sensor or sensors in the refinements above may be transmitted wirelessly via the transmitter/receiver and the antenna to a receiver for storage and/or processing. Moreover, data may also be transmitted wirelessly from an external transmitter via the antenna and the receiver to the microcontroller. Transmission is accomplished by means of electromagnetic waves.

BRIEF DESCRIPTION OF THE DRAWINGS

The principles of exemplary embodiments of the invention are depicted in the drawings and described in greater detail in the following.

DETAILED DESCRIPTION OF THE PREFERRED EMBODIMENTS

Figure 1:
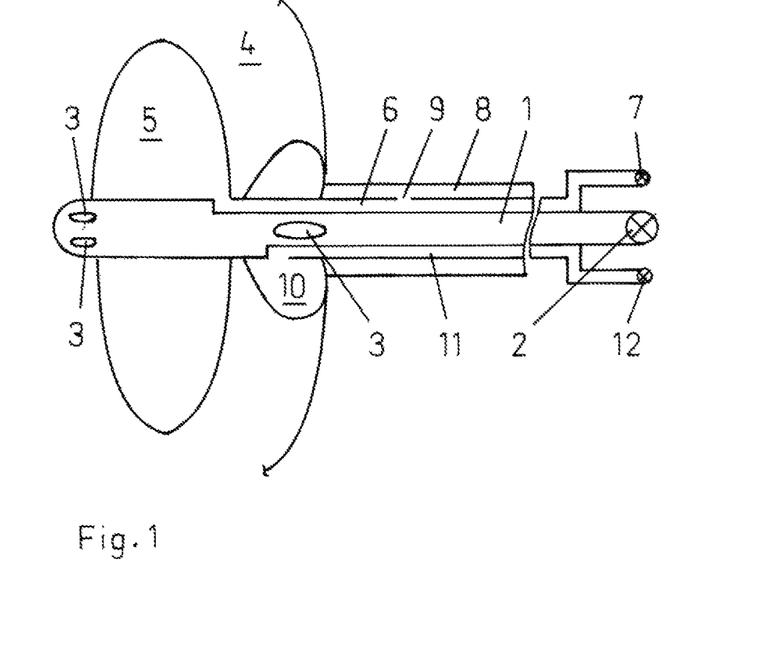
FIG. 1 depicts a urinary catheter.

In a first exemplary embodiment, a urinary catheter essentially comprises a catheter tube 1, a channel 6 as a first channel 6 having a reservoir container 5 and a second channel 11 having a retention device 10.

FIG. 1 depicts the principle of a urinary catheter.

The proximal end of the urinary catheter is disposed in the urinary bladder 4. The reservoir 5 container is filled with a fluid. The retention device 10 is positioned deep in the bladder trigone above the floor of the bladder and the prostate or the sphincter muscle of the bladder 4. A catheter eye 3 is positioned as close as possible to the bladder floor so that the bladder 4 may be completely emptied of urine. The catheter tube 1 has at least one outlet opening as a first connection 2 that is disposed at the distal end of the urinary catheter. The retention unit 10 is embodied like a balloon, the interior of which opens into a third connection 12, at the distal end, via the second channel 11. This urinary catheter has, for example, three catheter eyes 3, one catheter eye 3 being disposed at the level of the retention unit 10 and two other catheter eyes being disposed adjacent to one another at the proximal end of the urinary catheter. The reservoir container 5 is connected to a second connection 7 on the distal end via the first channel 6. This first channel 6 has at least one opening 9 that is embodied as a perforation. This opening 9 connects the first channel 6, connected to the reservoir container 5, to the inner wall of the urethra 8. Thus fluid from the reservoir container 5 travels to the inner wall of the urethra 8. To this end, the second connection 7 is closed. Advantageously, the urethra 8 is thus continuously flushed with fluid, so that bacteria do not accumulate and associated inflammation is prevented. The first channel 6 and the second channel 11 are arranged immediately at the catheter tube 1 and thus run parallel thereto.

Figure 2:
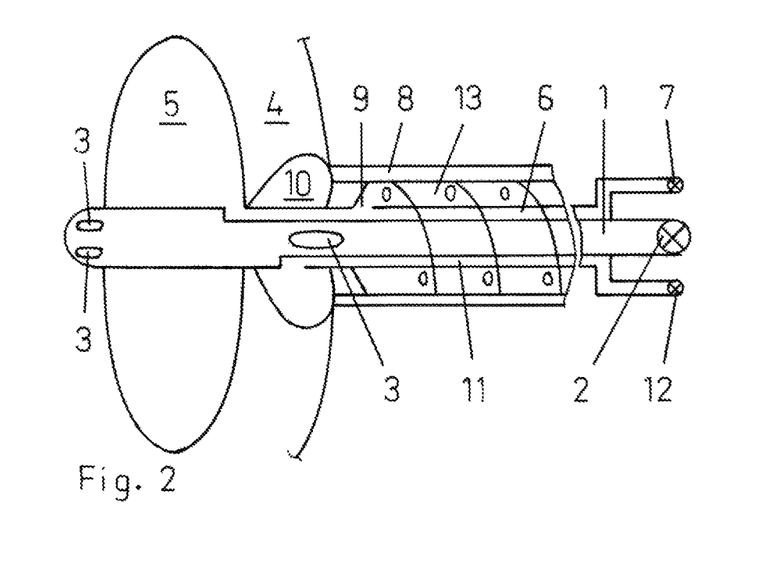
FIG. 2 depicts a urinary catheter having a membrane.

FIG. 2 depicts the principle of a urinary catheter having a membrane 13.

In a first embodiment, the urinary catheter furthermore has a membrane 13 that is disposed between catheter tube 1, with the first channel 6 and the second channel 11, and the urethra 8. Moreover, it is connected to the opening 9 of the first channel 6 so that fluid travels from the reservoir container 5 via the first channel 6 and the opening 9 into the membrane 13 and thus also to the inner wall of the urethra 8, so that the later is moistened.

Figure 3:
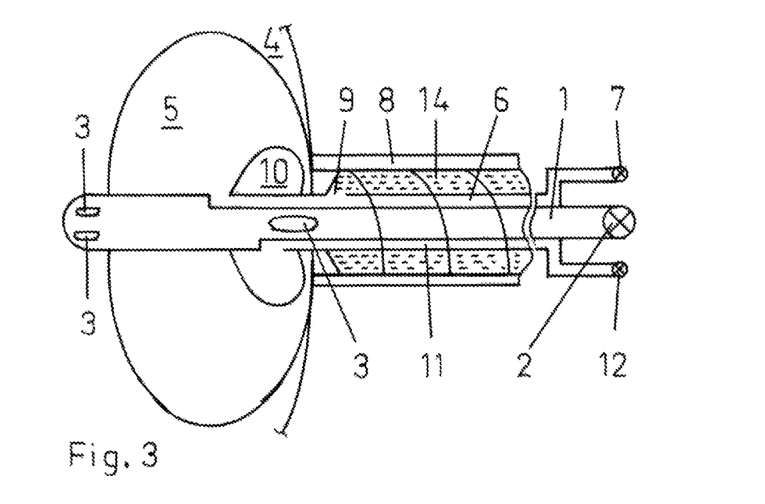
FIG. 3 depicts a urinary catheter having a sponge-like material.

FIG. 3 depicts the principle of a urinary catheter having a sponge-like material 14.

In a second embodiment, the urinary catheter furthermore has, instead of the membrane 13 in the first embodiment, a sponge-like material 14 that is disposed between the catheter tube 1, with the first channel 6 and the second channel 11, and the urethra 8. Moreover, it is connected to the opening 9, so that fluid from the reservoir container 5 is conducted via the first channel 6 and the opening 9 into the sponge-like material 14. Via the latter fluid travels out of the reservoir container 5 to the first channel 6 and via the opening 9 to the inner wall of the urethra 8, so that the latter is moistened. Due to the flexibility of the sponge-like material 14 and the sponge-like material 14 saturated with fluid, additional pressure and friction between the catheter tube 1, with the channels 6, 11, and the urethra 8 is prevented.

Figure 4:
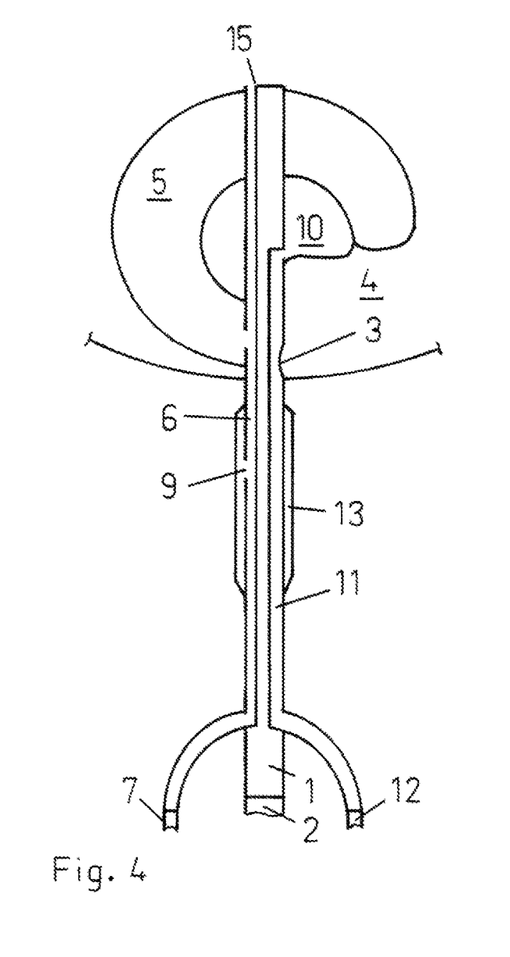
FIG. 4 depicts a urinary catheter having an additional flushing option for the bladder.

FIG. 4 depicts the principle of a urinary catheter having an additional option for flushing the bladder 4.

In a third embodiment, the first channel 6 terminates in the interior of the bladder 4, the end of the first channel 6 being open or having a membrane and/or a non-return device. The end 15 of the first channel 6 may be arranged on the proximal end of the urinary catheter. FIG. 4 depicts the urinary catheter in section, wherein the balloon-type reservoir container 5 and the balloon-type retention unit 10 have a cutout so that a catheter eye 3 is positioned just above the bladder floor and the bladder 4 may be completely emptied of urine.

For the purposes of example, FIG. 4 furthermore depicts the first channel 6 and the second channel 11 as components of the catheter tube 1. In their wall, the first channel 6 and/or the catheter tube 1 have a through-opening for connecting the urethra 8 to the reservoir container 5. The first channel 6 and the catheter tube 1 may be connected to one another, at least in the region of the opening, so that no fluid can travel out of the reservoir container 5 into the catheter tube 1. Naturally a region of the wall of the catheter tube 1 may also be a region of the first channel 6. The second channel 11 is arranged in the catheter tube 1 in the same way, it having at least one through-opening for connecting the second channel 11 to the proximal retention unit 10. Naturally a region of the wall of the catheter tube 1 may also be a region of the second channel 11.

The channels 6, 11 of the first embodiment and of the second embodiment may also be components of the catheter tube 1. To this end, the channels 6, 11 may be attached as separate tubes on the inner wall of the catheter tube 1.

Figure 5:
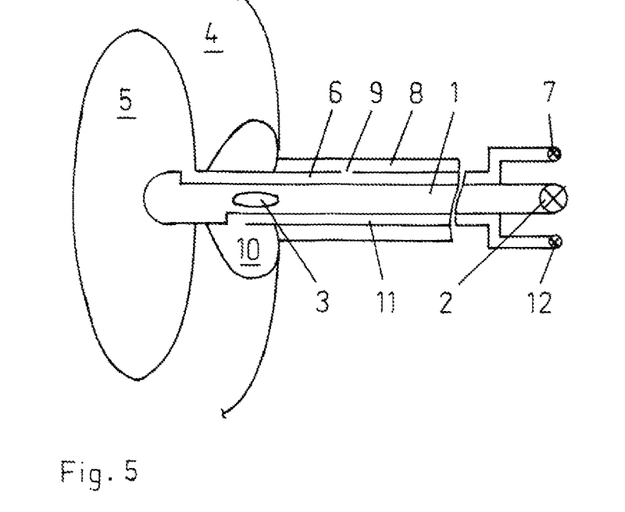
FIG. 5 depicts a urinary catheter having a retention unit and a reservoir container; and, FIG. 6 depicts a urinary catheter having a retention unit, a reservoir container, and a supply container.

In a second embodiment, a urinary catheter essentially comprises a catheter tube 1, a channel 6 as a first channel 6, with a reservoir container 5, and a second channel 11, with a retention unit 10.

FIG. 5 depicts the principle of a urinary catheter having a retention unit 10 and a reservoir container 5.

The proximal end of the urinary catheter is disposed in the urinary bladder 4. The reservoir container 5 is filled with a fluid. The retention unit 10 is positioned deep in the bladder trigone above floor of the bladder and the prostate or the sphincter muscle of the bladder 4. A catheter eye 3 is positioned as close as possible above the bladder floor so that the bladder 4 may be completely emptied of urine. The catheter tube 1 has at least one outlet opening as the first connection 2, and it is disposed at the distal end of the urinary catheter. Moreover, the catheter tube 1 terminates in the reservoir container 5. The retention unit 10 is embodied in a balloon-type manner, and its interior opens via the second channel 11 in a third connection 12 at the distal end. The reservoir container 5 is connected to a second connection 7 on the distal end via the first channel 6. This first channel 6 has openings 9 embodied as perforations. The openings 9 connect the first channel 6, connected to the reservoir container 5, to the inner wall of the urethra 8. Thus fluid from the reservoir container 5 travels on the inner wall of the urethra 8. To this end, the second connection 7 is closed. The urethra 8 is thus advantageously continuously flushed with fluid, so that bacteria do not accumulate and associated inflammation may be prevented. The first channel 6 and the second channel 11 are arranged immediately at the catheter tube 1 and thus run parallel thereto.

Figure 6:
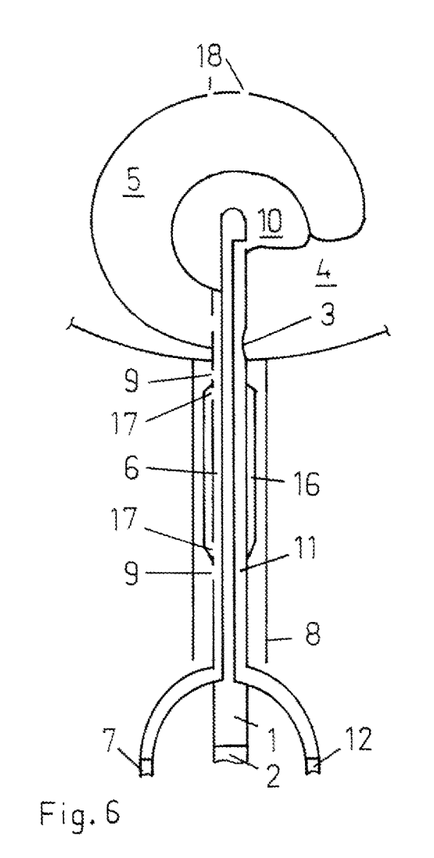

FIG. 6 depicts the principle of a urinary catheter having a retention unit 10, a reservoir container 5, and a supply container 16.

In a first embodiment, the urinary catheter furthermore has a supply container 16 that has a flexible wall and that is disposed between catheter tube 1, with the first channel 6 and the second channel 11, and the urethra 8. The openings 9 here are first openings 9, the supply container 16 being disposed between two first openings 9. The first channel 6 has second openings 17 in the region of the supply container 16. Thus when the reservoir container 5 is being filled, fluid simultaneously travels into the supply container 16. During moistening of the urethra 8, the reservoir container 5 empties first. The supply container 16 empties only thereafter, if the reservoir container 5 is not re-filled in the interim. The flexible wall of the supply container 16 may advantageously be embodied, at least in regions, as a selectively permeable membrane or a semi-permeable membrane. Thus the urethra 8 may also be moistened via this membrane.

In a further embodiment, the reservoir container 5 may have an outlet 18, embodied as a perforation, to the urinary bladder 4. However, at least one region of the wall of the reservoir container 5 may also be a selectively permeable membrane or a semi-permeable membrane.

In other embodiments of the exemplary embodiments:
at least one pressure sensor and/or one temperature sensor and/or one fluid level sensor may be disposed in the reservoir container 5,
at least one moisture sensor may be disposed in the first channel 6, and/or
at least one flow sensor may be disposed in the catheter tube 1 and/or in the first channel 6.

These may be connected, individually or collectively, to a microcontroller of a transponder having a transmitter/receiver and an antenna for electromagnetic waves.

LIST OF REFERENCE NUMERALS

1 Catheter tube
2 First connection
3 Catheter eye
4 Bladder
5 Reservoir container
6 First channel
7 Second connection
8 Urethra
9 Opening, first opening
10 Retention unit
11 Second channel
12 Third connection
13 Membrane
14 Sponge-like material
15 Open end of first channel
16 Supply container
17 Second opening
18 Outlet

The invention claimed is:

1. A urinary catheter comprising a catheter tube (1) with a first connection (2) at the distal end and at least one catheter eye (3), wherein at least one region of a wall of a reservoir container (5) is a selectively permeable membrane or a semi-permeable membrane, or the reservoir container (5) has at least one outlet (18), embodied as a perforation, to the urinary bladder (4), in that the reservoir container (5) is connected via a channel (6) to a second connection (7) as the distal end of the channel (6), and in that the channel (6) is configured to communicate with the urethra (8) via at least one opening (9) of a channel wall, so that the interiors of the channel and the urethra are configured to communicate, wherein configured to be disposed between the catheter tube (1), with the channel (6), and urethra (8), at least in regions, is a permeable membrane (15), a sponge-like material (14), a film having perforations, or a combination thereof, wherein fluid travels via the opening (9) as a perforation, when the second connection (7) is closed, out of the reservoir container (5) into the permeable membrane (13), the semi-permeable membrane, the sponge-like material (14), the film having perforations, or the combination thereof, wherein the reservoir container (5) is simultaneously a retention device of the urinary catheter or in that the urinary catheter has a retention apparatus or in that the proximal reservoir container (5) is disposed above a proximal retention unit (10) on the catheter tube (1), wherein the catheter eye (3) is disposed at the level of the retention unit (10), wherein the lower edge of the catheter eye (3) closes with the lower edge of the retention unit (10), so that, after the catheter has been inserted into the bladder, the catheter eye (3) is positioned directly above the sphincter muscle of the urethra at the floor of the urethra.

2. The urinary catheter according to claim 1, wherein the proximal reservoir container (5) surrounds, the proximal retention unit (10), at least in regions.

3. The urinary catheter according to claim 2, wherein the reservoir container (5) and the retention unit (10) are balloon-type hollow bodies.

4. The urinary catheter according to claim 2, wherein the channel (6) is a first channel (6), in that the proximal retention unit (10) is a balloon-type hollow body connected via a second channel (11), and in that the second channel (11) has a third connection (12) as the distal end thereof.

5. The urinary catheter according to claim 1, wherein a permeable membrane (13), a semi-permeable membrane, a sponge-like material (14), a film having perforations, or a combination thereof is disposed, at least in regions, between catheter tube (1), with the first channel (6) and the second channel (11), and urethra (8), wherein fluid travels out of the reservoir container (5) via the opening (9) as a perforation, with the second connection (7) closed, into the permeable membrane (13), the semi-permeable membrane, the sponge-like material (14), the film having perforations, or the combination thereof.

6. The urinary catheter according to claim 1, wherein the channel (6) is configured to communicate with the urethra (8) via at least two openings (9) of the channel wall, and disposed between the openings (9) is a supply container (16) that surrounds the catheter tube (1), at least in regions, that is connected to the first channel (6) by two openings (17), and that has a flexible wall.

7. The urinary catheter according to claim 6, wherein the flexible wall of the supply container (16) has, at least in regions, a selectively permeable membrane or a semi-permeable membrane or has perforations and/or in that an open-pore flexible body may be disposed in the supply container (16).

8. The urinary catheter according to claim 1, wherein the channel (6) is configured to terminate in the interior of the bladder (4), the end (15) being open and or having a membrane and/or a non-return device.

9. The urinary catheter according to claim 1, wherein a proximal retention unit (10) comprises a balloon, the balloon having a cutout up to the catheter tube (1) so that the cross-section of the balloon is an interrupted ring, and in that the catheter tube (1) has the catheter eye (3) in the cutout.

10. The urinary catheter according to claim 1, wherein at least one pressure sensor and/or one temperature sensor and/or one fluid level sensor is disposed in the reservoir container (5) and/or in the catheter tube (1), and in that the pressure sensor and/or the temperature sensor and/or the fluid level sensor is connected to a microcontroller of a transponder having a transmitter/receiver and an antenna for electromagnetic waves.

11. The urinary catheter according to claim 1, wherein at least one moisture sensor is disposed in the first channel (6) and in that the moisture sensor is connected to a microcontroller of a transponder having a transmitter/receiver and an antenna for electromagnetic waves.

12. The urinary catheter according to claim 1, wherein at least one flow meter is disposed in the catheter tube (1) and/or in the first channel (6) and in that the flow sensor is connected to a microcontroller of a transponder having a transmitter/receiver and an antenna for electromagnetic waves.

* * * * *